United States Patent [19]

Louie et al.

[11] Patent Number: 4,663,026
[45] Date of Patent: May 5, 1987

[54] SOLVENT EXTRACTION AND PURIFICATION OF ACID SOLUBLE OIL FROM AN HF ALKYLATION UNIT

[75] Inventors: Yuk-Mui Louie, Philadelphia, Pa.; Fred S. Zrinscak, Woodbury Heights, N.J.

[73] Assignee: Mobil Oil Corporation, New York, N.Y.

[21] Appl. No.: 772,577

[22] Filed: Sep. 4, 1985

Related U.S. Application Data

[63] Continuation-in-part of Ser. No. 675,495, Nov. 28, 1984, abandoned.

[51] Int. Cl.$^4$ ............................................. C10G 17/00
[52] U.S. Cl. ................................. 208/262; 208/113; 208/131; 585/710; 585/719; 585/723
[58] Field of Search ..................... 208/262, 113, 131; 585/710, 719, 723

[56] References Cited

U.S. PATENT DOCUMENTS

2,574,006  11/1951  Allen ................................ 260/683.4
3,726,940  4/1973  Cannady et al. ............... 260/683.48
4,199,409  4/1980  Skraba ................................... 203/39
4,373,110  2/1983  Hutson, Jr. .......................... 585/719
4,404,418  9/1983  Hutson, Jr. et al. ................ 585/710
4,454,369  6/1984  Hutson, Jr. et al. ................ 585/719

Primary Examiner—Curtis R. Davis
Attorney, Agent, or Firm—Alexander J. McKillop; Michael G. Gilman; Malcolm D. Keen

[57] ABSTRACT

A process for recovering HF catalyst and acid soluble oil from an HF alkylation unit acid stream containing HF and acid soluble oils. The acid stream is charged to a distillation column, wherein free HF acid, and stripping fluid added to the column, are removed as an overhead fraction. A bottoms fraction is removed from this column containing acid soluble oil and some HF. This bottoms fraction is cooled and mixed with a light hydrocarbon, and the mixture is allowed to settle. The mixture separates into an HF-lean acid soluble oil, plus solvent upper phase and an HF-rich acid soluble oil lower phase. The HF-lean phase may be withdrawn from the process as a product or upgraded to improve its quality, permitting recycle of the HF-rich phase with reduced acid soluble oil content, to the alkylation unit.

23 Claims, 4 Drawing Figures

SOLVENT EXTRACTION AND PURIFICATION OF ACID SOLUBLE OIL FROM AN HF ALKYLATION UNIT

RELATED APPLICATIONS

This application is a continuation-in-part of U.S. patent application Ser. No. 675,495 filed Nov. 28, 1984, and now abandoned.

BACKGROUND OF THE INVENTION

1. Field of the Invention

This invention relates to an improvement in an HF alkylation process, and particularly to an improved method of recovering hydrofluoric acid and acid soluble oil from a mixture containing HF acid, used as a catalyst in the process, and acid soluble oil, an undesirable by-product of the process.

2. Description of the Prior Art

It is common practice in the petroleum industry to produce high octane motor fuel by alkylating isoparaffins with olefins in the presence of a catalyst, which preferably is hydrofluoric acid or hydrogen fluoride (HF). The effluent from the alkylation reactor is usually passed to a settling vessel wherein a hydrocarbon phase is separated from an HF acid phase. The hydrocarbon phase is fractionated to separate low boiling hydrocarbons from the alkylate product. The acid phase is cooled and recycled to the alkylation reactor for use in the alkylation process. However, it is necessary to purify a portion of the recycled acid phase in order to control a buildup of acid soluble oils (hereinafter referred to as ASO) and water in the system. Generally, this purification is accomplished by passing a portion of an HF-containing stream from the settler to an HF purification or rerun fractionation column, wherein HF is stripped from the ASO by means of a vaporous hydrocarbon, which is preferably isobutane. While the HF purification systems employed heretofore have generally been effective to produce an acid stream having the required purity, the recovered ASO stream from the purification unit usually has contained undesirable amounts of HF, resulting in the loss of valuable HF and in ecology problems. This has required subsequent purification steps to remove HF before thE ASO can be processed further, such as by recycling to the refinery as fuel, or passed to a disposal unit. Typical alkylation processes are shown in U.S. Pat. No. 2,574,006 issued to Allen, and U.S. Pat. No. 3,726,940 issued to Cannady et al.

An improved method of controlling acid soluble oil in the circulating HF acid stream used in an HF alkylation process is disclosed in U.S. Pat. No. 4,199,409, the teachings of which are incorporated herein by reference. In this patent, a conventional HF acid rerun column is used to strip a portion of the HF acid stream from circulating acid containing ASO. The acid soluble oil stream obtained as a bottoms fraction in the rerun column is cooled and allowed to separate into two phases. The lower phase, which preferably comprises 75 to 90% of the material, is removed as a bottoms fraction from the separator. The lower phase is relatively rich in HF, while the upper phase in the separator is almost HF acid free. The patentee recognized that the heavy acid soluble oil streams are difficult to separate in practice, and that to achieve complete phase separation would require prohibitively long separation times or a prohibitively large separator vessel.

Another method of recovering acid soluble oil is disclosed in U.S. Pat. No. 4,404,418, the teachings of which are incorporated herein by reference. In this patent, the HF acid containing ASO is heated, by any means suitable to generate heat, wherein the lower boiling HF is removed overhead as vapor, and the higher boiling ASO is separated out and remains in liquid form and is removed as product from the HF rerun column. This acid soluble oil is cooled and then diluted with liquid isobutane recovered from the upper liquid hydrocarbon phase in the settler, which was changed to a separation zone. The diluted acid soluble oil in isobutane is then charged to a separation zone, where any remaining HF catalyst is driven off. The recovered acid soluble oils dissolved in isobutane are then sent to the HF alkylation zone in an amount required to ensure production of a quality HF alkylation product.

Other attempts to separate ASO from a portion of the HF phase are disclosed in U.S. Pat. Nos. 4,373,110 and 4,454,369, the disclosures of which are herein incorporated by reference. In U.S. Pat. No. 4,373,110, at least a portion of the ASO is combined with at least a portion of the hydrocarbon phase for an alkylation unit. In U.S. Pat. No. 4,454,369, ASO is separated from HF acid catalyst in a fractionation zone by heating the fractionation zone with a condensable stream comprising liquid and vaporous components. In the process of condensation, latent heat is evolved which is used to effectuate the separation of ASO and HF acid catalyst, and dilution of the separated ASO is achieved with the use of the produced condensate.

The present applicants reviewed the work that others have done in cleaning up the circulating acid stream in an HF alkylation plant and recovering the acid soluble oil, but were not able to find any completely satisfactory solution. Acid-containing streams are extremely corrosive on the processing equipment, requiring specialized metal alloys and increasing the capital cost of the equipment. Simply neutralizing the HF acid containing in an acid soluble oil stream, obtained from the bottom of a conventional HF acid rerun column to minimize corrosion, represented a needless loss of the HF acid contained in this stream. The solution proposed in U.S. Pat. No. 4,199,409, while an improvement, required a difficult phase separation before the process could be successfully implemented.

Simply cooling the HF acid-soluble oil stream withdrawn from the bottom of an HF acid rerun column was not a good way to produce a two-phase mixture, because of the difficulty of separating the two phases which formed after cooling. The concentration gradient obtained by simple cooling was excellent. U.S. Pat. No. 4,199,409 reported that the HF-rich phase contained approximately 150 times as much acid, on a weight percent basis, as to the HF-lean phase. The problem was the difficult phase separation.

Cooling the acid soluble oil and the diluting with liquid isobutane, as proposed in U.S. Pat. No. 4,404,418, did not address the problem of corrosion of the equipment, since the diluted ASO was fed directly to subsequent processing equipment, such as an isostripper, without phase separation.

Settling for less concentration gradient, or differential in HF concentration between the HF-lean ASO and the HF-rich ASO, would be more than compensated by the ease in phase separation afforded by addition of a relatively light hydrocarbon stream or equivalent solvent to the acid soluble oil stream withdrawn from the bottoms of a conventional HF acid rerun column, while at the same time avoiding the corrosion problems present in prior art processes.

SUMMARY OF THE INVENTION

Accordingly, the present invention provides a method of recovering hydrofluoric acid and the acid soluble oil from a mixture containing HF and an acid soluble oil, and controlling the ASO concentration in the reactor, said method comprising stripping said mixture with a vaporous hydrocarbon in a fractionation column; recovering as an overhead product from said column a majority of said HF and said vaporous hydrocarbon fed to said column; removing a bottoms fraction from said column comprising acid soluble oil with a reduced HF concentration, as compared to the HF concentration in said feed mixture; mixing said bottoms fraction with a light hydrocarbon solvent and cooling to a temperature below 60° C. and sufficient to induce a phase separation; separating in a phase separation means an upper phase and a lower phase, wherein said upper phase is relatively lean in HF concentration and said lower phase is relatively rich in HF concentration; and recovering said upper phase with a relatively lean HF content as a product of the process.

It is to be understood that sufficient amounts of water are also present in the HF-rich (lower) phase. However, for convenience in description, reference to the HF-rich (lower) phase hereinafter will also be understood to include a phase containing a significant concentration of water.

In an alternative embodiment, the product value of the oil containing the upper (relatively lean HF content) phase can be upgraded by sending it to an isostripper, where the oil is recovered with the alkylate product. This stream can be added to the reactor effluent (isostripper feed) or fed separately to the isostripper. Alternatively, it can be sent to storage or other processing units, such as an FCC or a coker. Corrosion problems in the isostripper or other units is significantly reduced by the use of the HF-lean (upper) phase. Thus, the oil can be processed in other units without caustic treatment and results in greater flexibility of processing conditions, while reducing corrosion of subsequent units.

In another embodiment, the present invention provides a method of recovering hydrofluoric acid from a circulating acid stream used to provide a source of HF acid in an HF alkylation plant, said circulating acid stream containing a mixture of HF and acid soluble oil, said method comprising charging a portion of said circulating acid stream to a feed point of an HF acid rerun column intermediate between an upper portion and a lower portion; charging to said column below said upper portion of said column a stripping hydrocarbon which strips out at least a portion of the HF acid from the HF acid-soluble oil feed, to said column; recovering as an overhead product from said upper portion a mixture of HF and stripping hydrocarbon; removing from said lower portion a bottoms fraction comprising a majority of the acid soluble oil in the mixture of HF and acid soluble oil charged to said column; mixing said bottoms fraction with a light hydrocarbon solvent and cooling said fraction to a temperature below 60° C. and sufficient to induce two liquid phases to form; and charging said cooled, two-phase stream into a separation zone to produce an upper liquid phase and a lower liquid phase, wherein said lower liquid phase contains at least twice as much HF acid, on a weight percent basis, as does said upper liquid phase; recycling at least a portion of said lower liquid phase, to said HF acid rerun column; removing said upper liquid phase from said separator as a product; and further processing the product to obtain an upgraded product.

DETAILED DESCRIPTION OF THE INVENTION

The basic building blocks of an HF alkylation unit are well known in the art.

The operation of an HF acid rerun column is disclosed in U.S. Pat. No. 4,199,409, the teachings of which have already been incorporated by reference. As disclosed in that patent, a slipstream of the circulating HF catalyst is withdrawn from the HF alkylation reactor and charged to an HF acid rerun column. The function of the rerun column is to recover and return purified HF to the system and remove acid soluble oil from the circulating HF catalyst. The acid soluble oil is removed by stripping HF acid from the HF-ASO mixture. The concentrated ASO is recovered as a bottoms fraction from the column, but this bottoms fraction still contains significant quantities of HF, much of which, if not all, must be removed from the ASO before the ASO can be burned, or sent to other units for further processing within the refinery without causing ecological or corrosion problems.

The operation of an HF alkylation unit is disclosed in U.S. Pat. No. 4,373,110, the teaching of which have already been incorporated by reference. As disclosed in that patent, a slipstream for withdrawing catalyst from the alkylation reactor is fed to a fractionator or rerun column. The fractionator is employed to separate polymeric material from the alkylation catalyst. Water and polymeric material withdrawn from the fractionator are mixed with the hydrocarbon (upper) phase of a settler and fed to a fractionator provided with a reboiler. Hydrogen product is withdrawn from a lower portion of this fractionator. Hydrogen fluoride and light hydrocarbons, such as propane, are withdrawn from an upper portion of the fractionator. The light hydrocarbon and hydrogen fluoride issuing from the fractionator are condensed and passed to an accumulator, where the mass separates into an upper light hydrocarbon phase and a lower HF liquid phase. Light hydrocarbon from the accumulator may be fed to the fractionator to provide light hydrocarbon reflux. The remainder of the light hydrocarbon is fed to a fractionator or stripper provided with reboiling means. Withdrawal of overhead light hydrocarbon and bottoms of recycle HF catalyst liquid is also described by patentee.

However, none of the aforementioned patents provide facile separation of HF-rich and lean phases with reduction in the corrosive effect of process streams.

In the present invention, the HF-ASO mixture withdrawn from the bottom of the acid rerun column is mixed with a light solvent, preferably a light hydrocarbon (HC), such as some fraction of the alkylate stream. Alkylate is the preferred light solvent. However, other light hydrocarbons, such as isobutane, as is disclosed in U.S. Pat. No. 4,404,418 previously incorporated by reference, could be used as the light solvent.

The advantage of using alkylate is its availability in the process and that it will also be more effective in phase separation than heavier molecular weight HC and easier to handle from processing standpoint than lighter HC. Also, other solvents such as benzene or kerosene would be contaminants in the system.

Preferably, the solvent is mixed with the HF-ASO stream from the bottom of the HF column while the HF-ASO stream is relatively hot. An unexpected advantage of mixing while hot is that the HF-ASO is a much easier stream to mix with when it is hot and fluid than when it is cold and viscous.

Regardless of whether or not the HF-ASO is hot when mixed with solvent, the mixture of HF-ASO plus solvent should be cooled, eventually to 10°-60° C., preferably about 20°-50° C., and charged to a phase separator.

Depending on the temperature of the HF-ASO stream, and on the amount of solvent that is added to this stream, various amounts of mixing may be required. Suitable mixing may be effected through the use of a low efficiency centrifugal pump, or passing these streams, in admixture, through one or more partially closed valves. Alternatively, stirred mixers, or in-line mixing valves, may be used. More exotic mixing devices, such as fiber film contactors, rotating disc contactors, and the like, may be used, but usually the increase in extraction efficiency will not justify the added cost of these more exotic contacting devices.

The volume ratio of solvent to HF-ASO stream will usually be in the range of 0.1-10, preferably around 0.5-1, volumes of solvent per volume of HF-ASO.

The cooling of the solvent/HF-ASO mixture may be accomplished by any conventional means. Indirect heat-exchange will give good results. Where process conditions warrant it, it is possible to cool the HF-ASO mixture withdrawn from the bottom of the HF acid rerun column by direct injection of relatively cool solvent. The cool solvent will mix with and cool the HF-ASO mixture.

It may be desirable to provide some mixture of direct and indirect cooling of these streams, e.g., indirect heat-exchange of the hot HF-ASO mixture withdrawn from the bottom of the column, followed by direct injection of relatively cold hydrocarbon solvent, followed by further indirect heat-exchange of the solvent/HF-ASO mixture.

Once the solvent/HF-ASO are mixed and cooled, they are allowed to separate into an upper HF-lean phase and a lower HF-rich phase. Phase separation may be enhanced by the use of coalescing devices, such as electrostatic precipitators, or simply by using a relatively large vessel. Phase separation is not hard to achieve in our process, as compared to the prior art processes, because the acid soluble oil is much easier to work with in a plant when diluted with a solvent.

The upper HF-lean phase is further processed to upgrade the quality of the product.

Figure 1:
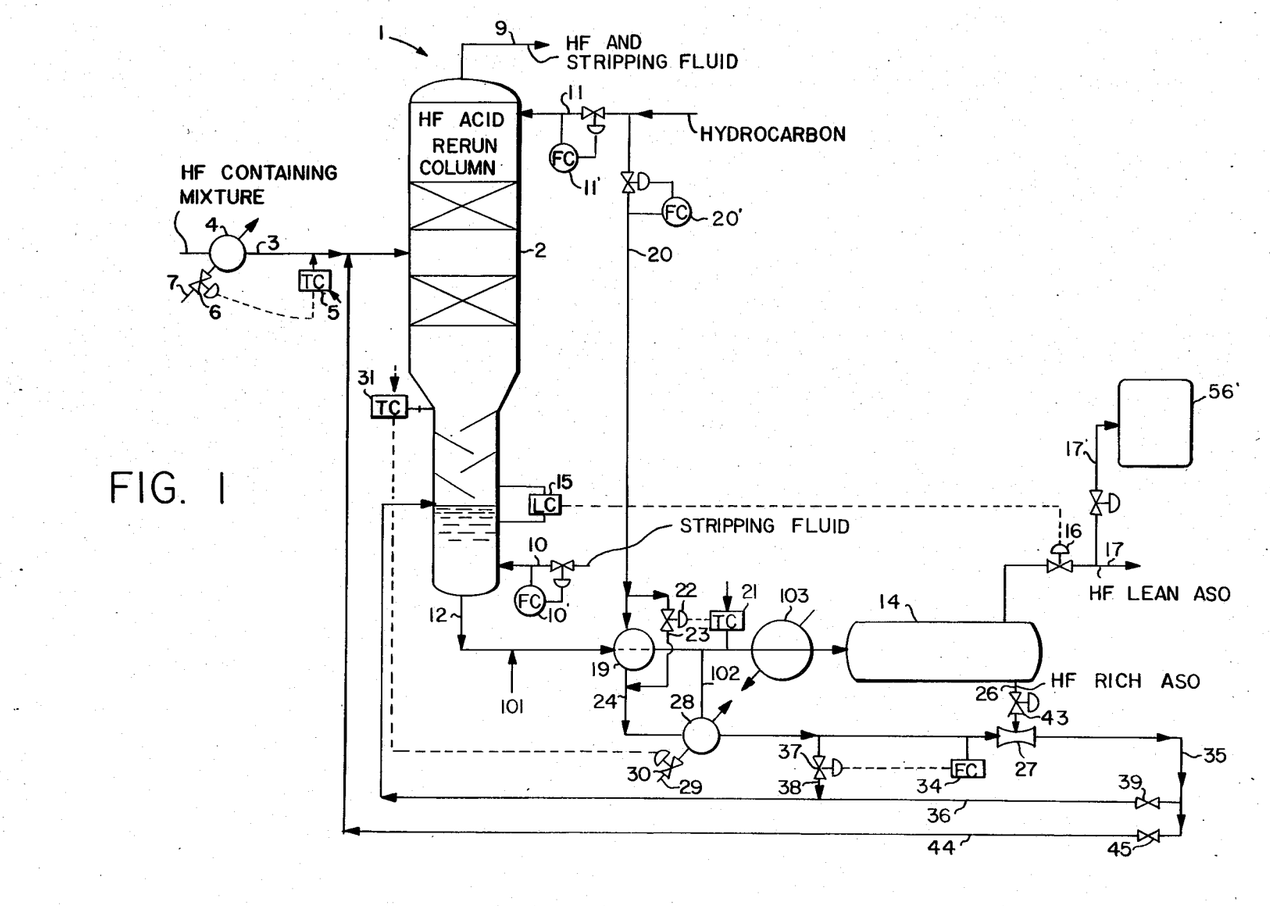
FIG. 1 is a schematic representation of a process used to recover HF from an HF alkylation unit circulating acid stream.

The present invention can be better understood by referring more in detail to FIG. 1.

Acid purification section 1 contains HF acid rerun column 2. The HF-ASO mixture withdrawn from the HF alkylation unit is charged through heater 4 and line 3 into column 2.

Stripping hydrocarbon is added to column 2 via lines 10 and 11, as regulated by flow controllers 10' and 11'. HF acid and stripping fluid are removed overhead from column 2 via line 9. Removed as a bottoms stream from HF acid rerun column 2 is an HF-ASO stream in line 12. Stripping hydrocarbon could also be added to the column at other points intermediate those previously discussed.

In the prior art processes, the HF-ASO mixture in line 12 was merely cooled by indirect heat-exchange and charged to phase separator 14. In the present invention, this relatively hot HF-ASO stream in line 12 is mixed with a solvent, either before cooling, in which case solvent is added via line 101, or after cooling, in which case solvent is added via line 102. Additional cooling of the HF-ASO plus solvent mixture may occur using indirect heat-exchanger 103. The cooled mixture of solvent/HF-ASO then enters separator 14. An HF-lean acid soluble oil phase, and most of the solvent added to the process, are removed from separator 14 via line 17. The heavy, HF-rich acid soluble oil phase which collects at the bottom of phase separator 14 is removed via line 26.

A large portion of this stream of HF-rich ASO is preferably recycled to the HF acid rerun column for added recovery of the HF contained therein. It may be diluted with additional stripping hydrocarbon, or additional solvent prior to recycle to rerun column 2. When dilution of this material with stripping hydrocarbon is desired, the stripping hydrocarbon may be added via line 24 and flow controller 34, with mixing of the HF-rich ASO and the stripping hydrocarbon occurring in educator 27, followed by recycle of this mixture to an upper portion of column 2 via lines 35 and 44, or to a lower portion of column 2 via lines 35 and 36.

Figure 4:
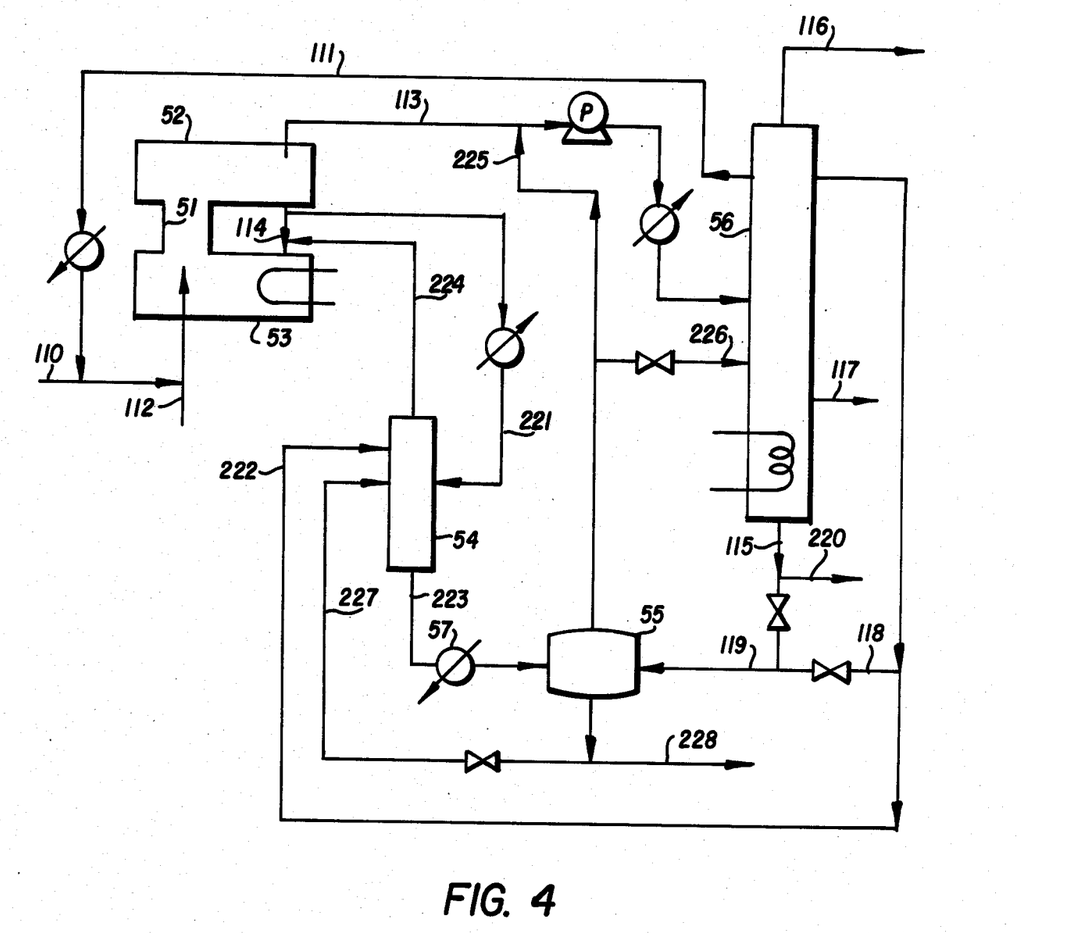
FIG. 4 is a schematic representation of a process for conducting an alkylation process recovering alkylate product, including regeneration of alkylate catalyst.

In an alternative embodiment in FIG. 4 is illustrated an HF alkylation process wherein an alkylation unit is illustrated, comprising an alkylation reactor 51 which includes means for regeneration of alkylation catalyst, shown generally at 54, including means 56 for recovery of alkylate product.

An olefin feed 110, which may also contain some paraffins, combine with recycle isobutane 111 and isobutane makeup 112, which are then introduced into the alkylation reactor 51. In the reactor 51, the hydrocarbon mixes with the catalyst (hydrofluoric acid) from the acid cooler 53. The reactor effluent is then sent to acid settler 52, where the major portion of the hydrocarbon 113 is separated from the acid 114. The hydrocarbon 113 from the acid settler 52 is sent to the fractionator 56 for recovery of the alkylate product 115. The alkylate product 220 can be sent to the motor gasoline pool or to an alkylate splitter to separate the total alkylate into light and heavy alkylate. The alkylate product 119 can also be routed for use within the process, i.e., as the solvent used to mix with the bottoms stream 223 from the regeneration 54, which is fed to separator 55. Lighter product 116 from the fractionator 56 is sent to other process units, known to those familiar with the state of the art, for recovery and treating of the lighter product.

Typical of such units are the accumulator and fractionator of the aforementioned U.S. Pat. No. 4,373,110, which has already been incorporated herein by reference. N-butane 117 is sometimes withdrawn from the fractionator 56 to meet product vapor pressure.

A major portion of the acid 114 from the acid settler 52 is sent to the acid cooler 53. A slipstream of spent acid 221 from the acid settler 52 is sent to the acid regenerator 54 to be stripped with isobutane 222, to recover an acid stream 224 with higher purity, to be sent back to the acid cooler 53 or combine with stream 114 from acid settler 52 before entering the acid cooler 53. The bottoms 223 from the acid regenerator is then cooled by means 57 and combined with isobutane 118 and/or alkylate 119 in mixer/settler vessel 55, which will provide for mixing and phase separation as previously described. The HF-free hydrocarbon phase 225 from this vessel 55 is combined with the reactor effluent 113 and sent to the fractionator 56. The HF-free hydrocarbon stream 226 can also be sent directly to the fractionator 56. This step will recover the hydrocarbon that otherwise will be discarded as ASO and recover acid in the form of organic fluoride. The organic fluoride will easily decompose to HF again in the fractionator 56. The bottoms 228 from the mixer/settler vessel 55, essentially free of hydrocarbon, can be:

processed offsite to separate the water and HF; or
neutralized with lime and disposed of as solid CaF for reprocessing to HF.

The bottoms stream 228 is easier to handle than ASO stream 223, from state-of-the-art acid regenerator 54, because the HF-water phase does not contain much hydrocarbon that can form sludge in the neutralization step. Alternatively, the HF-water phase 227 can be sent back to the acid regenerator 54 to recover the acid.

As can be seen from the embodiment of FIG. 1, the much lower corrosive HF-lean (upper) phase removed via line 17 can be fed directly to downstream processing means 56'. This downstream processing means 56' can be an isostripper which is fed directly by line 17 or, alternatively, line 17 can be mixed with the reactor effluent (isostripper feed). Other downstream processing units 56' could be an FCC, a coker or intermediate storage tanks. The stream exiting line 17' can also be sent directly to a product stream, thus increasing yield. Ratio of the HF-lean (upper) phase exiting line 17 to HF-rich (lower) phase exiting line 26 is typically 70:30, although this ratio is not critical. It is noted that the effluent of line 17, comprising the HF-lean (upper) phase, contains little or no water. Thus, the downstream processing means 56' will not be subject to highly corrosive activity, as in the prior art, since only the (upper) HF-lean phase is processed. As in the embodiment of FIG. 4, the (lower) HF-rich phase may be recycled to the rerun column or processed offsite to separate the water and HF or neutralized with lime and disposed of as solid CaF.

The temperature level controls shown in the drawings are not critical. Temperature controller 31 may adjust the heat added to the recycled HF-rich ASO, as shown in the drawings, or temperature controller could adjust the amount of stripping fluid added via line 20.

Similarly, liquid withdrawn from the bottom of column 2 via line 12 could be on flow control, with a level controller in separator 14 used to adjust the amount of HF-lean ASO withdrawn from the plant. If this is done, level controller 15 might adjust flow of hydrocarbon in line 20 to hold a constant liquid level in the bottom of column 2.

In the process of the present invention, the ratio of the acid concentration in the upper phase in settler 14 to that of the lower phase, is not nearly as great as the ratio claimed in the prior art patent, 0.1 wt % HF in the upper phase to 14.6 wt % HF in the lower phase. What is possible is relatively easy separation of these two phases.

To clarify the difference between our process and the prior art processes, a number of calculated examples are presented hereinafter.

Particle Dynamics (5-61) *Perry's Handbook* using Stoke's Law and terminal settling velocity.

$$U_T = \frac{gdp^2(\rho_p - \rho)}{18\mu}$$

where $U_T =$ terminal settling velocity of particle $P$ $g =$ acceleration due to gravity (9.81 m$^2$/sec)

$dp =$ diameter of spherical particle $P$ (660 microns = 0.002165 ft)

$\rho_p =$ density of particle $P$ $\rho =$ density of continuous fluid $\mu =$ viscosity of continuous fluid Pure *HF*

$\rho = 58.8$ lb/ft$^3$ at 100° F.

$\mu = 0.25$ cs at 100° F.

Water $\rho = 61.94$ lb/ft$^3$ at 100° F.

$\mu = 0.65$ cp at 100° F.

ASO $\rho = 59.69$ lb/ft$^3$ at 60° F.

$\mu = 66.3$ cs at 130° F.

Alkylate $\rho = 43.6$ lb/ft$^3$ at 60° F.

$\mu = 0.6$ cs at 100° F.

Aqueous *HF 50/50*

$\rho = 60.37$ lb/ft$^3$ at 100° C.

*HF*/Water to be Separated from ASO at 100° F.

$$U_T = \frac{gdp^2(\rho_p - \rho)}{18\mu}$$

$$U_T = \frac{32.17 \text{ ft/sec}^2 \times (0.002165)^2 \text{ft}^2 (60.37 - 59.69 \text{ lb/ft}^3)}{\frac{59.69 \text{ lb}}{\text{ft}^3} \times 18 \times 66.3 \times 10^{-2} \frac{\text{cm}^2}{\text{sec}} \times 1.076 \times \frac{10^{-3} \text{ ft}^2/\text{sec}}{\text{cm}^2/\text{sec}}}$$

$U_T = 0.000134$ ft/sec $= 0.0963$ in/min

*HF*/Water to be Seperated from ASO/3/1 Dilution

With Alkylate at 100° F.

-continued $$U_T = \frac{gdp^2(\rho_p - \rho)}{18\mu}$$

3/1 Dilution ASO/alkylate = 10 cs at 100° F.

3/1 Dilution ASO/alkylate = 55.67 lb/ft³

$$U_T = \frac{32.17 \text{ ft/sec}^2(0.002165 \text{ ft})^2(60.37 - 55.67 \text{ lb/ft}^3)}{\frac{55.67 \text{ lb}}{\text{ft}^3} \times 18 \times 10 \times 10^{-2} \frac{\text{cm}^2}{\text{sec}} \times 1.076 \times \frac{10^{-3}\text{ft}^2/\text{sec}}{\text{cm}^2/\text{sec}}}$$

$U_T$ = 0.006573 ft/sec = 4.7325 in/min

This is also consistent with what applicants saw in the laboratory, very distinct separation within one-half hour.

HF/Water to be Separated from ASO/1/1 Dilution with Alkylate at 100° F.

$$U_T = \frac{gdp^2(\rho_p - \rho)}{18\mu}$$

1/1 Dilution ASO/alkylate = 2.8 cs at 100° F.

1/1 Dilution ASO/alkylate = 51.64 lb/ft³

$$U_T = \frac{32.17 \text{ ft/sec}^2(0.002165 \text{ ft})^2(60.37 - 51.64 \text{ lb/ft}^3)}{18 \times 2.8 \times 10^{-2} \frac{\text{cm}^2}{\text{sec}} \times \frac{51.64 \text{ lp}}{\text{ft}^3} \times 1.076 \times \frac{10^{-3}\text{ft}^2/\text{sec}}{\text{cm}^2/\text{sec}}}$$

$U_T$ = 0.047 ft/sec = 2.82 ft/min

These calculations can be summarized as follows:

1. Assuming 660 micron (0.002165 ft) size droplet/

No dilution;

Settling velocity = 0.0963 in/min of acid from ASO

2. Assuming 660 micron droplet/Diluted with 1/3 alkylate/ASO:

Settling time = 4.7 in/min

3. Assuming 660 micron (0.002165 ft) droplet/

Diluted 1/1 alkylate/ASO:

Settling time = 2.82 ft/min

LAB EXPERIMENTS

Based on lab experiments, there was no noticeable change in HF concentration gradient between the present invention and prior art processes. Acid concentration of the HF-rich phase is essentially the same as the rerun column bottom stream before dilution and separation. The acid is probably just saturated (<1.0%) in the upper oil phase.

From these examples, it can be seen that the process of the present invention significantly reduces the capital cost of the phase separator necessary to separate an HF-lean ASO from an HF-rich ASO, since unduly large separators permitting long residence time are not required. The practice of the present invention permits removal of significant amounts of acid-soluble oil, with only minimal loss of HF acid from the system. Based on the ratio of settling velocities, the dilution settling of the present invention permits use of a settler with only about 1/50th or less of the cross-sectional area of prior art processes.

Further, as noted in the following Table, showing typical corrosion rates for various concentrations of HF/H₂O/ASO/alkylate mixtures, corrosion can be severe with only small quantities of HF acid.

TABLE 1

Corrosion Rates for Carbon Steel in HF/H₂O/ASO/Alkylate Mixtures

| Solution Composition | | | | Corrosion Rate, mpy | | |
|---|---|---|---|---|---|---|
| % Alkylate | % ASO | % Reagent Grade HF (50% H₂O) | Temp. ° F. Purge Gas | 200 Air | 200 N₂ | 300 N₂ |
| 0 | 0 | 100 | Liquid | 212 | — | 732 |
|   |   |   | Vapor | 190 | — | 146 |
| 25 | 0 | 75 | Liquid | 396 | — | 388 |
|   |   |   | Vapor | 82 | — | 112 |
| 50 | 0 | 50 | Liquid | 318 | — | 354 |
|   |   |   | Vapor | 65 | — | 59 |
| 75 | 0 | 25 | Liquid | 55 | — | 177 |
|   |   |   | Vapor | 16 | — | 12 |
| 100 | 0 | 0 | Liquid | 0.7 | — | 0.4 |
|   |   |   | Vapor | 0.5 | — | 0.3 |
| 0 | 40 | 60 | Liquid | 359 | — | 475 |
|   |   |   | Vapor | 95 | — | 35 |
| 0 | 60 | 40 | Liquid | 123 | — | 310 |
|   |   |   | Vapor | 39 | — | 19 |
| 0 | 80 | 20 | Liquid | 83 | — | 154 |
|   |   |   | Vapor | 17 | — | 12 |
| 0 | 90 | 10 | Liquid | 53 | — | 43 |
|   |   |   | Vapor | 18 | — | 6 |
| 0 | 100 | 0 | Liquid | 0.1 | — | 0.4 |
|   |   |   | Vapor | 0.1 | — | 0.4 |

Figure 2:
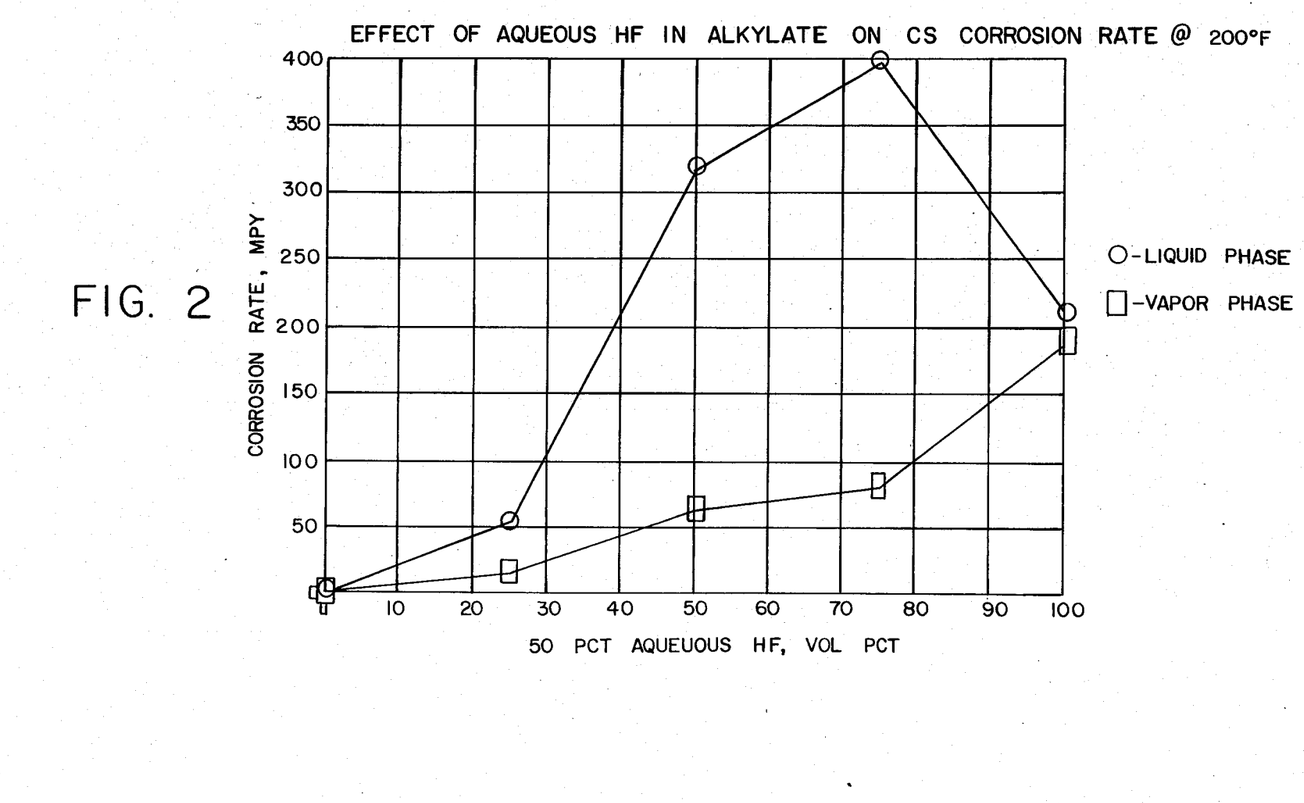
FIG. 2 illustrates the corrosion rate on stainless steel of aqueous HF in alkylate.
Figure 3:
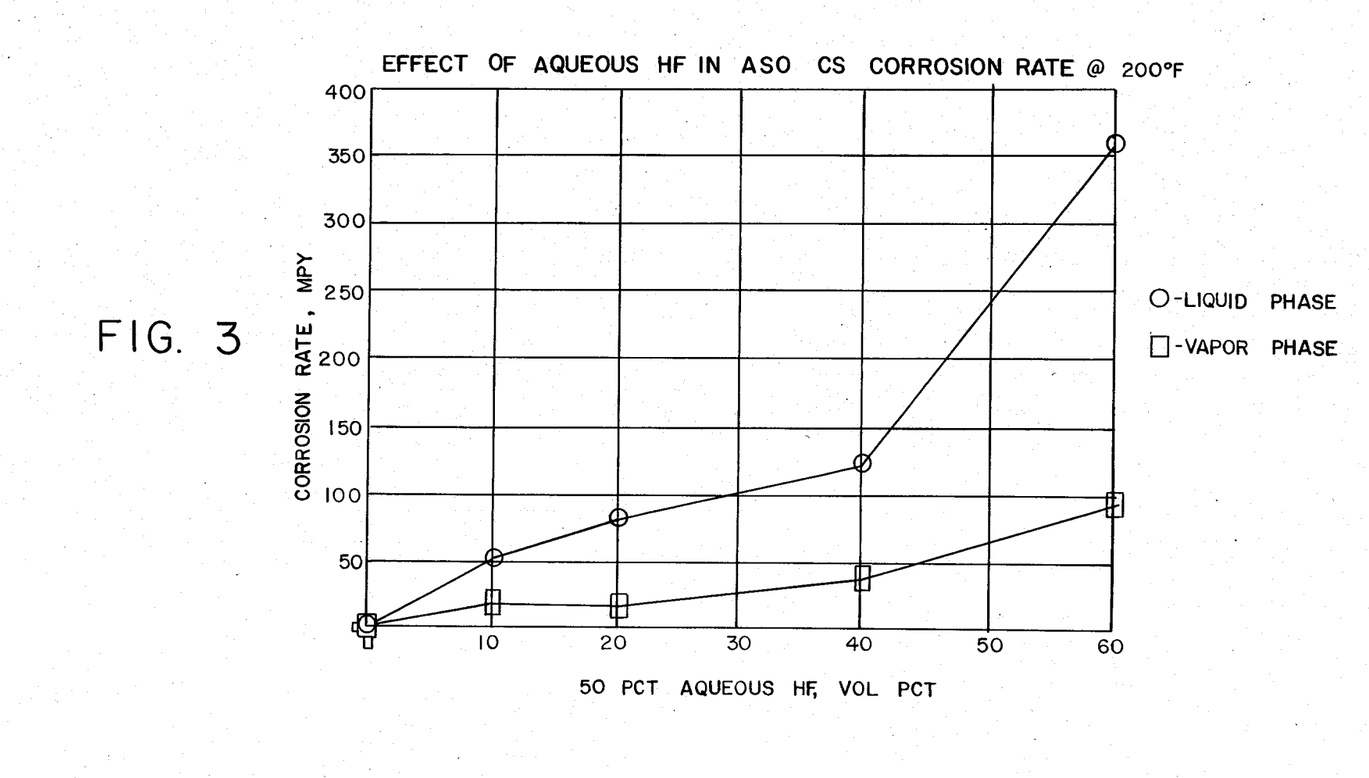
FIG. 3 illustrates the corrosion rate on stainless steel of aqueous HF in ASO.

The corrosion rate on carbon steel of aqueous HF in alkylate is shown for both vapor and liquid phase in attached FIG. 2. The corrosion rate on carbon steel of aqueous HF in ASO is shown in attached FIG. 3.

It can thus be seen that the present process minimizes corrosion without caustic treatment of the HF stream. Utilizing solvent dilution and phase separation subsequent urgrading of an HF containing oil phase can be achieved with reduced corrosion of equipment. Yields and quality of the product are both increased with corrosion of processing equipment reduced and controlled within tolerable limits.

We claim:

1. A method of recovering hydrofluoric acid and acid soluble oil from a mixture containing HF and ASO, said method comprising:
   (i) stripping said mixture with a vaporous hydrocarbon in a fractionation column;
   (ii) recovering as an overhead product from said column a majority of said HF and said vaporous hydrocarbon fed to said column;
   (iii) removing a bottoms fraction from said column comprising acid soluble oil with a reduced HF concentration, as compared to the HF concentration in said feed mixture;
   (iv) mixing said bottoms fraction with a light hydrocarbon solvent and cooling to a temperature below 60° C. and sufficient to induce a phase separation;
   (v) separating in a phase separation means an upper phase and a lower phase, wherein said upper phase is relatively lean in HF concentration and said lower phase is relatively rich in HF concentration; and
   (vi) recovering said upper phase with a relatively lean HF content as a product.

2. The method of claim 1, wherein said bottoms fraction is removed from said column at a temperature of 150° to 250° C., is mixed with a light hydrocarbon selected from the group of isobutane and motor fuel alkylate obtained from an HF alkylation unit, at a temperature of 50° to 150° C., followed by cooling of said mixture to a temperature of 10° to 60° C., to induce phase separation.

3. The method of claim 1, wherein the volume ratio of light hydrocarbon solvent to heavy bottoms fraction is about 0.3:1 to 10:1.

4. The method of claim 1, wherein said light hydrocarbon solvent is isobutane and the volume ratio of isobutane to said heavy bottoms stream is about 0.5:1 to 1:1.

5. The process of claim 1, wherein said light hydrocarbon solvent is motor fuel alkylate and the volume ratio of alkylate to said heavy bottom stream is 0.1:1 to 1:1.

6. The process of claim 1, wherein said lower phase which is relative rich in HF is recycled to said column.

7. The method of claim 1, wherein said lower phase which is relatively rich in HF is charged to an HF alkylation plant.

8. The method of claim 1, including the step of feeding the product of step (vi) to downstream processing means.

9. The method of claim 8, wherein the step of feeding comprises feeding to an isostripper.

10. The method of claim 8, wherein the step of feeding comprises feeding to an FCC unit.

11. The method of claim 8, wherein the step of feeding comprises feeding to a coker.

12. The method of claim 8, wherein the step step of feeding comprises feeding the product directly without caustic treatment thereof.

13. A method of recovering hydrofluoric acid from a circulating acid stream used to provide a source of HF acid in an HF alkylation plant, said circulating acid stream containing a mixture of HF and an acid soluble oil, said method comprising:
 (i) charging a portion of said circulating acid stream to a feed point of an HF acid rerun column intermediate between an upper portion and a lower portion;
 (ii) charging to said column below said upper portion of said column a stripping hydrocarbon which strips out at least a portion of the HF acid from the HF acid-soluble oil feed to said column;
 (iii) recovering as an overhead product from said upper portion a mixture of HF and stripping hydrocarbon;
 (iv) removing from said lower portion a bottoms fraction comprising a majority of the acid soluble oil in the mixture of HF and acid soluble oil charged to said column;
 (v) mixing said bottoms fraction with a light hydrocarbon solvent and cooling said fraction to a temperature below 60° C. and sufficient to induce two liquid phases to form;
 (vi) charging said cooled, two-phase stream into a separation zone to produce an upper liquid phase and a lower liquid phase, wherein said lower liquid phase contains at least twice as much HF acid, on a weight percent basis, as does said upper liquid phase;
 (vii) recycling at least a portion of said lower liquid phase to said HF acid rerun column; and
 (viii) removing said upper liquid phase from said separator as a product.

14. The process of claim 13, wherein said light hydrocarbon solvent is selected from the group of isobutane and motor fuel alkylate stream obtained from an HF alkylation unit.

15. The process of claim 13, wherein said solvent is isobutane.

16. The process of claim 13, wherein said light solvent is a motor fuel alkylate.

17. The process of claim 13, wherein the volume ratio of said light hydrocarbon to said bottoms fraction is 0.1:1 to 10:1.

18. The process of claim 17, wherein said volume ratio is about 0.3:1 to 1:1.

19. The process of claim 13, including the step of feeding the product of step (viii) to a downstream processing means.

20. The process of claim 19, wherein the step of feeding comprises feeding to an isostripper.

21. The process of claim 19, wherein the step of feeding comprises feeding to an FCC unit.

22. The process of claim 19, wherein the step of feeding comprises feeding to a coker.

23. The process of claim 19, wherein the step of feeding comprises feeding the product directly without caustic treatment.

* * * * *